(12) United States Patent
Sakai (10) Patent No.: US 7,938,778 B2
(45) Date of Patent: May 10, 2011

(54) ULTRASOUND DIAGNOSIS APPARATUS (75) Inventor: Ryoichi Sakai, Mitaka (JP)

(73) Assignee: Aloka Co., Ltd., Tokyo (JP)

( * ) Notice: Subject to any disclaimer, the term of this patent is extended or adjusted under 35 U.S.C. 154(b) by 636 days.

(21) Appl. No.: 11/964,161

(22) Filed: Dec. 26, 2007

(65) Prior Publication Data
US 2009/0171200 A1 Jul. 2, 2009

(51) Int. Cl.
*A61B 8/00* (2006.01)
(52) U.S. Cl. ...................................... 600/437; 600/438
(58) Field of Classification Search .................. None
See application file for complete search history.

(56) References Cited

U.S. PATENT DOCUMENTS

| | | |
|---|---|---|
| 5,368,044 A | 11/1994 | Cain et al. |
| 5,474,070 A | 12/1995 | Ophir et al. |
| 5,524,636 A | 6/1996 | Sarvazyan et al. |
| 5,678,565 A | 10/1997 | Sarvazyan |
| 5,902,240 A | 5/1999 | Ishii et al. |
| 6,079,255 A | 6/2000 | Binnig et al. |
| 6,132,376 A | 10/2000 | Hossack et al. |
| 6,270,459 B1 | 8/2001 | Konofagou et al. |
| 6,520,913 B1 | 2/2003 | Pesavento et al. |
| 7,107,159 B2 | 9/2006 | German |
| 2002/0056312 A1 | 5/2002 | Tamura et al. |
| 2002/0103432 A1 | 8/2002 | Kawchuk |
| 2002/0157478 A1 | 10/2002 | Seale |
| 2004/0234113 A1 | 11/2004 | Miga |
| 2006/0074311 A1 | 4/2006 | Sakai et al. |
| 2006/0120582 A1 | 6/2006 | Squilla et al. |
| 2006/0184020 A1 | 8/2006 | Sumi |
| 2006/0241447 A1 | 10/2006 | Harada et al. |

FOREIGN PATENT DOCUMENTS

| | | |
|---|---|---|
| EP | 0737441 A1 | 10/1996 |
| JP | 9-84788 A | 3/1997 |
| JP | 2001-309918 A | 11/2001 |
| JP | 2004-298205 A | 10/2004 |
| JP | 2005-152079 A | 6/2005 |
| JP | 2005-160704 A | 6/2005 |
| WO | 02/24075 A1 | 3/2002 |

OTHER PUBLICATIONS

Office Action of U.S. Appl. No. 10/951,322, dated Oct. 18, 2007.
Office Action of U.S. Appl. No. 10/951,322, dated Mar. 28, 2007.
U.S. Appl. No. 11/835,819, filed Aug. 8, 2007.
U.S. Appl. No. 11/869,238, filed Oct. 9, 2007.
Notice of Grounds for Rejection dated Jul. 27, 2010, issued in corresponding Japanese Patent Application No. 2005-172363.

*Primary Examiner* — Long V Le
*Assistant Examiner* — Nicholas L Evoy
(74) *Attorney, Agent, or Firm* — Westerman, Hattori, Daniels & Adrian, LLP (57) ABSTRACT A surface point tracked by an echo tracking processor unit for each ultrasonic beam is a tracking point. A strain measurement unit measures an amount of strain of a bone based on the surface points. A delay time measurement unit measures a time for the amount of strain of the bone to reach a return reference value, corresponding to a state before a load is applied, after the load is first applied to the bone and then removed.

14 Claims, 7 Drawing Sheets

ULTRASOUND DIAGNOSIS APPARATUS

BACKGROUND

1. Technical Field

The present invention relates to an ultrasound diagnosis apparatus, and in particular to an ultrasound diagnosis apparatus used for diagnosis of a hard tissue such as a bone.

2. Related Art

Simple quantitative measurement of mechanical characteristics such as bone strength is desired for diagnosing bone metabolic diseases such as osteoporosis, for judging fracture risk, and for quantitatively diagnosing bone union after treatment of bone fracture.

The evaluation of bone formation and bone union depends largely on X-ray photography, but quantitatively diagnosing bone strength by means of X-ray photography is very difficult. As a method of measuring bone strength in the related art, there is known a strength test of a sample bone of a measurement target. However, this method requires an extraction operation for obtaining a sample bone, and the method is thus invasive. A method of measuring an amount of bone and a bone density has employed devices such as general-purpose X-ray CT and DXA (dual-energy X-ray absorptiometry). However, these devices are merely means for measuring the amount of bone and cannot provide an evaluation of bone strength. Moreover, in light of the fact that tissue is irradiated with X-rays in these methods, these methods cannot be considered non-invasive.

Other attempts to quantitatively evaluate bone strength include a strain gauge method in which a strain gauge is mounted on an external fixator and the strain of the external fixator is measured; a vibration wave method in which a vibration is applied to a bone from the outside and a characteristic frequency is evaluated; and an acoustic emission method in which acoustic waves generated by a bone which has reached yield stress are detected. These methods, however, suffer from various problems in that a limitation is imposed on the treatment to which these methods can be applied, that the bone is subjected to invasion, and that evaluation precision is insufficient.

In view of the above circumstances, the inventors of the present invention have proposed an ultrasound diagnosis apparatus for noninvasively and quantitatively evaluating the mechanical characteristics of bone (refer to, for example, Japanese Patent Publication JP 2004-298205 A).

The ultrasound diagnosis apparatus described in JP 2004-298205 A forms a plurality of ultrasonic beams on a bone, obtains a plurality of echo signals corresponding to the individual ultrasonic beams to specify a surface point corresponding to the bone surface for each echo signal, and generates shape data of the bone surface on the basis of the plurality of surface points obtained from the plurality of echo signals. Then, a mechanical characteristic of the bone is evaluated on the basis of a change in the shape data when an external load is applied to the bone. Thus, the apparatus is an epoch-making technology capable of noninvasively and quantitatively evaluating the mechanical characteristics of a bone in a living organism from the shape data of the bone surface on the basis of the echo signals.

The inventors of the present invention have further improved the epoch-making technology described in JP 2004-298205 A and have studied methods of more precisely evaluating the mechanical characteristic of a hard tissue such as the bone. In particular, the present inventors have studied evaluation of the bone as a viscoelastic structure in consideration that the bone which is a representative example of a hard tissue is a viscoelastic structure simultaneously having an elastic characteristic and a viscous characteristic.

SUMMARY

The present invention was conceived in view of the above-described circumstances, and an advantage of the present invention is that an ultrasound diagnosis apparatus is provided which can evaluate viscoelasticity of a hard tissue such as a bone.

According to one aspect of the present invention, there is provided an ultrasound diagnosis apparatus comprising a transmission and reception unit which forms an ultrasonic beam on a hard tissue and obtains an echo signal, a surface detecting unit which detects a plurality of surface points corresponding to a surface of the hard tissue based on the echo signal, a shape value measurement unit which measures a shape value reflecting a shape of the hard tissue based on the plurality of detected surface points, and an evaluation value measurement unit which measures an evaluation value of a mechanical characteristic of the hard tissue based on a return change of the shape value from a state in which an external action is applied to the bone to a state after the external action is removed.

In this aspect of the present invention, the shape value reflecting the shape of the hard tissue is a value reflecting the form and state occurring outside of the hard tissue such as the bone, and is, for example, an amount of strain of the hard tissue surface or an amount of displacement of the hard tissue surface. The shape value changes when an external action such as a load is applied to the hard tissue. If the hard tissue has a viscosity in addition to the elasticity, the shape value changes with a delay of the change in the external action. In the above-described structure, the evaluation value is measured based on the return change (degree of the delay) of the shape value after the external action is removed. In other words, the measured evaluation value reflects the viscoelasticity of the hard tissue. As a result, with the ultrasound diagnosis apparatus of the above-described structure, the viscoelasticity of the hard tissue can be evaluated.

BRIEF DESCRIPTION OF THE DRAWINGS

An exemplary embodiment of the present invention will be described in detail based on the following figures, wherein.

DETAILED DESCRIPTION

A preferred embodiment of the present invention will now be described.

Figure 1:
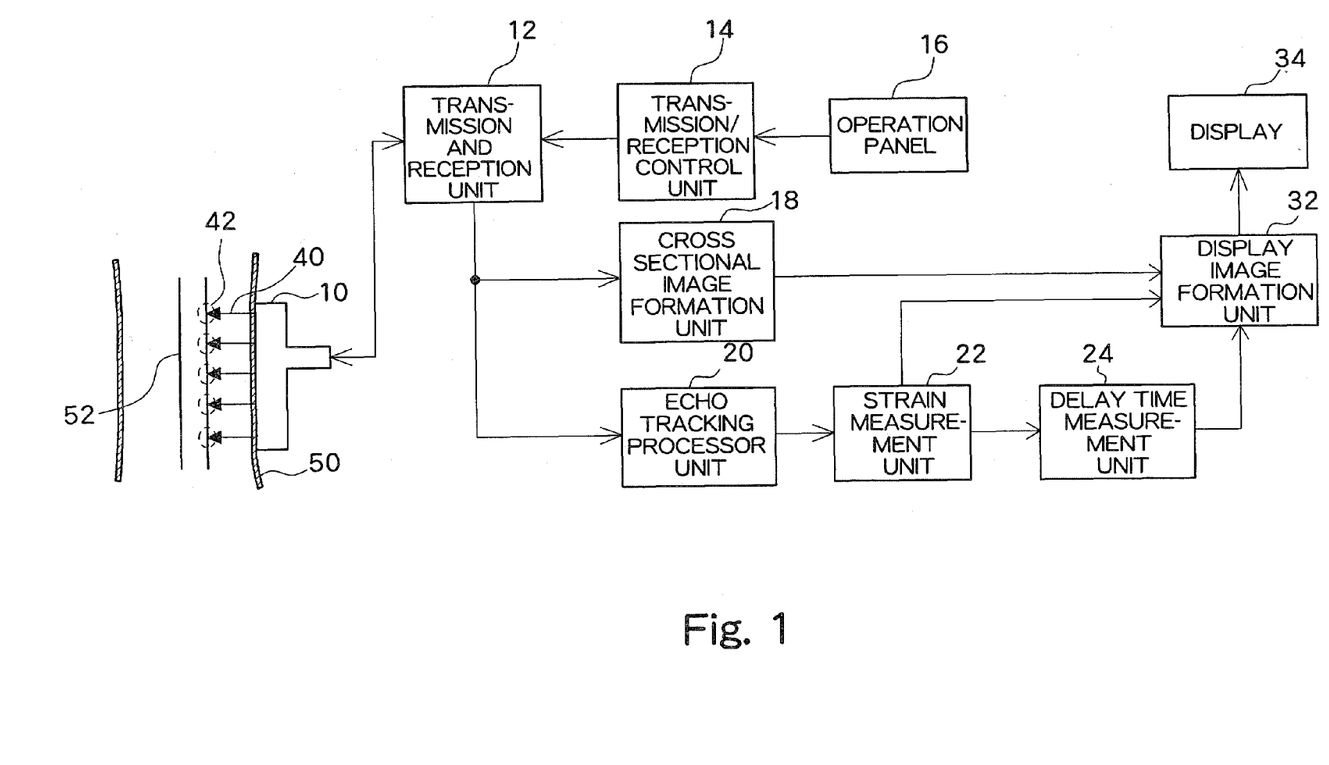
FIG. 1 is an overall structural diagram of an ultrasound diagnosis apparatus according to a preferred embodiment of the present invention.

FIG. 1 shows a preferred embodiment of an ultrasound diagnostic apparatus according to the present invention. FIG. 1 is a diagram showing an overall structure of the ultrasound diagnostic apparatus. A probe 10 is an ultrasonic probe which is preferably used in contact with a surface of the body of a subject 50. Alternatively, an ultrasonic probe which is inserted into the subject may be used. The probe 10 forms ultrasonic beams 40 towards a bone 52 within the body of the subject 50. As the probe 10, it is desirable to use a linear electronic scan probe (linear probe) which electronically scans the ultrasonic beam 40. Alternatively, the probe 10 may be a probe which uses a method such as a sector electronic scanning. The bone 52 to be diagnosed may be, for example, a tibia or a fibula. Tracking points 42 which are set on the bone 52 will be described later in more detail.

A transmission and reception unit 12 controls the probe 10 and electronically scans the ultrasonic beam 40 on a cross sectional surface (a cut surface of a subject 50 in FIG. 1). When the probe 10 is a linear probe, for example, sequential electronic scanning of 120 ultrasonic beams 40 (FIG. 1 only shows five ultrasonic beams for echo tracking which will be described later) is applied and an echo signal is obtained for each ultrasonic beam 40. The plurality of obtained echo signals are output to a cross sectional image formation unit 18 and the cross sectional image formation unit 18 forms a cross sectional image (B mode image) of the bone based on the plurality of echo signals.

The echo signal obtained in the transmission and reception unit 12 is also output to an echo tracking processor unit 20. The echo tracking processor unit 20 applies an echo tracking process in which the bone surface portion is extracted from each echo signal and is tracked. For the echo tracking process, for example, a technique detailed in JP 2001-309918 A is used. For the echo tracking process, for example, five tracking echo signals are used. The tracking echo signals may be selected from among the echo signals used for forming a cross sectional image (for example, 120 echo signals) or may alternatively be obtained by forming five tracking echo signals separately from the beams for forming the cross sectional image.

The five ultrasonic beams 40 shown in FIG. 1 are beams for obtaining tracking echo signals. An examiner inputs an instruction related to transmission/reception of the ultrasound through an operation panel 16 to a transmission/reception control unit 14 and the transmission/reception control unit 14 controls the transmission and reception unit 12 based on the instruction from the examiner. With this structure, ultrasonic beams 40 for obtaining tracking echo signals are transmitted to a diagnosis site on the bone surface according to the instruction from the examiner. In the transmission/reception of ultrasound, a strong reflected wave is obtained from the bone surface. Therefore, the echo signals obtained from within the body of the subject are obtained as having large amplitude in a portion corresponding to bone surface.

Figure 2:
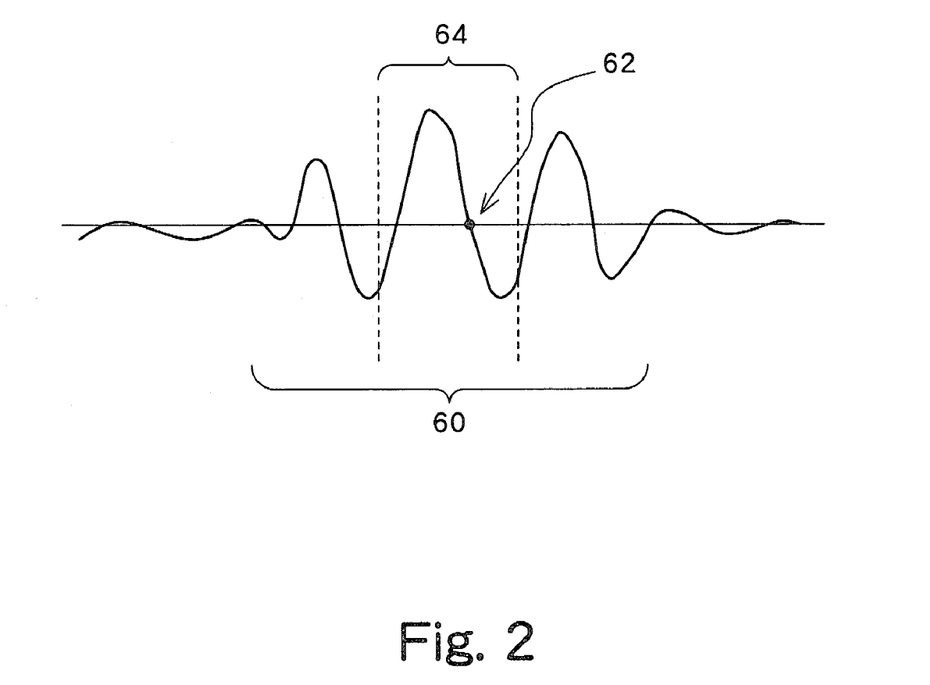
FIG. 2 is a schematic view showing a bone surface portion of each echo signal.

FIG. 2 is a diagram schematically showing a bone surface portion of an echo signal. As shown in FIG. 2, each echo signal includes a range 60 within which the echo signal has a large amplitude corresponding to the bone surface. When the bone surface portion is considered simply as a portion having a large amplitude, it is unclear as to which portion within the range 60 corresponds to the surface portion and, as a result, an extraction error approximately equal to the range 60 is caused. In the echo tracking process, a zero-cross point 62 is detected as a representative of each echo signal, and the detected zero-cross point 62 is tracked so as to significantly increase the precision of the extraction.

The zero-cross point 62 is detected as a timing, within a tracking gate period 64, at which the polarity of the echo signal is inverted from positive to negative or from negative to positive. In FIG. 2, the zero-cross point 62 is a timing at which the polarity of the echo signal is inverted from positive to negative. When the zero-cross point 62 is detected, a new tracking gate is set with the detected zero-cross point 62 as its center. In the echo signal obtained next from the same point, a zero-cross point 62 is detected within the newly set tracking gate period 64. In this manner, a zero-cross point 62 is tracked as the surface point for each echo signal.

Figure 3A:
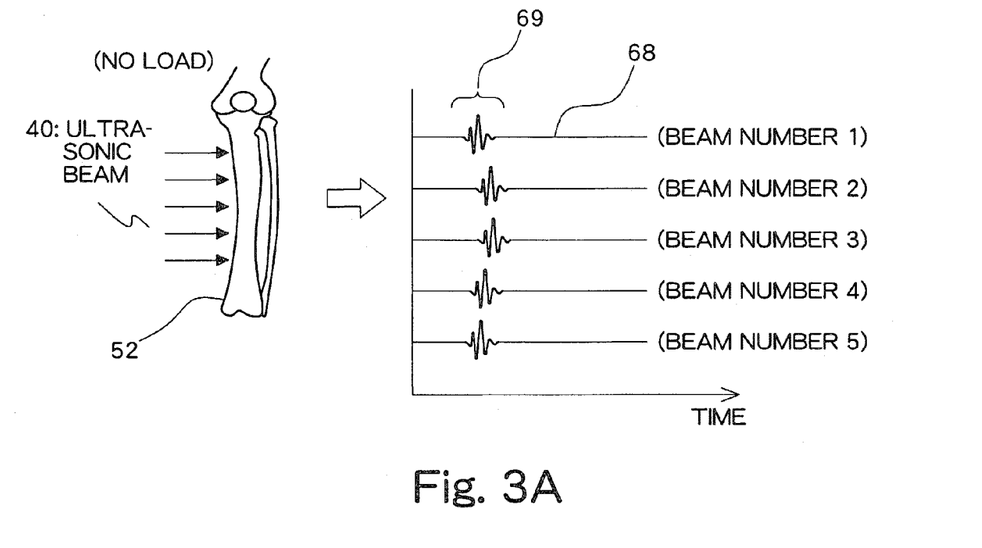
FIGS. 3A and 3B are diagrams for explaining tracking of a bone surface portion.
Figure 3B:
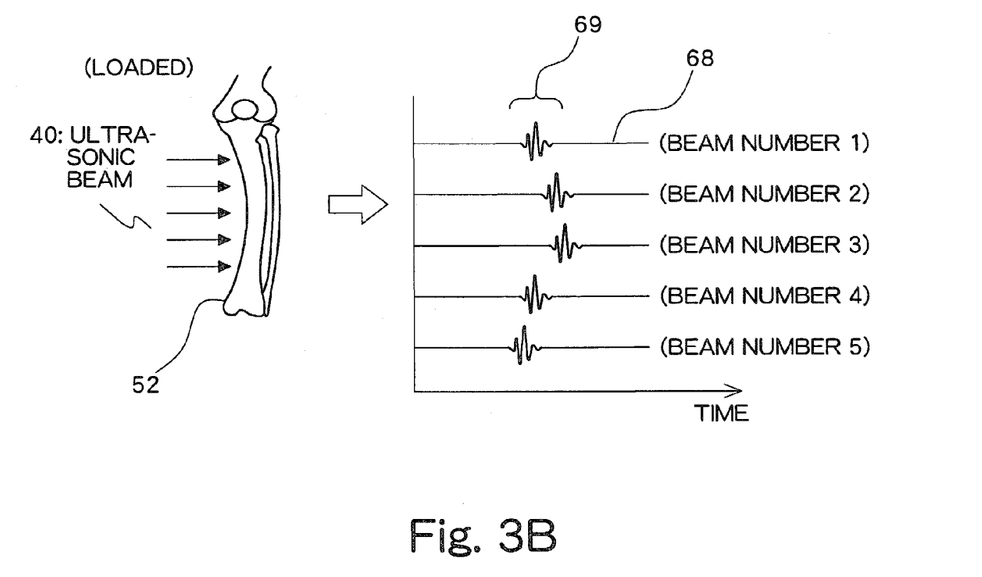

FIGS. 3A and 3B are diagrams for explaining tracking of a bone surface portion by five echo signals. In the ultrasound diagnosis apparatus of the present embodiment, an amount of strain of a bone is measured as a shape value reflecting the shape of the bone. The amount of strain of the bone can be determined, for example, based on a displacement in a surface point between a reference state (a state in which no load is applied to the bone: no-load) and a measurement state (for example, a loaded state: loaded). In the present embodiment, a displacement is measured from the reference state of the surface point for each echo signal (each ultrasonic beam).

FIG. 3A is a diagram showing tracking of a bone 52 in the no-load state. The echo signals 68 corresponding to the five ultrasonic beams 40 directed to the bone 52 have large amplitudes (amplitude maximum section 69) at a portion corresponding to the bone surface. The five ultrasonic beams 40 are assigned beam numbers 1-5 from the top to the bottom in the figure. Because a zero-cross point (reference numeral 62 in FIG. 2) is detected as a surface point in the amplitude maximum section 69 for each ultrasonic beam, the position of the bone surface is very precisely identified.

FIG. 3B is a diagram showing tracking of the bone 52 in the loaded state. Similar to FIG. 3A, the echo signals 68 corresponding to the five ultrasonic beams 40 directed to the bone 52 have large amplitudes (amplitude maximum section 69) at a portion corresponding to the bone surface. Because a load is applied, the bone 52 in FIG. 3B has a larger strain (larger flexure of bone) compared to the bone 52 of FIG. 3A. Although a configuration with five echo tracking echo signals is exemplified in FIGS. 3A and 3B, the measurement can be made with a plurality of signals having the number other than 5.

Referring again to FIG. 1, in the echo tracking processor unit 20, the surface point which is tracked for each echo signal, that is, for each ultrasonic beam 40 is the tracking point 42. A strain measurement unit 22 measures, for each ultrasonic beam 40, a displacement in a surface point (tracking point 42) between a reference state (no-load state) and a measurement state (for example, loaded state) and measures displacements of the surface points from the five ultrasonic beams 40. In other words, for each of the ultrasonic beams of beam numbers 1-5 in FIGS. 3A and 3B, an amount of movement of the zero-cross point between the no-load state and the loaded state is measured as the displacement. As a result, displacement values for five points on the bone surface are obtained. The strain measurement unit 22 calculates an amount of strain of the bone based on the displacements of the five points on the bone surface.

Figure 4:
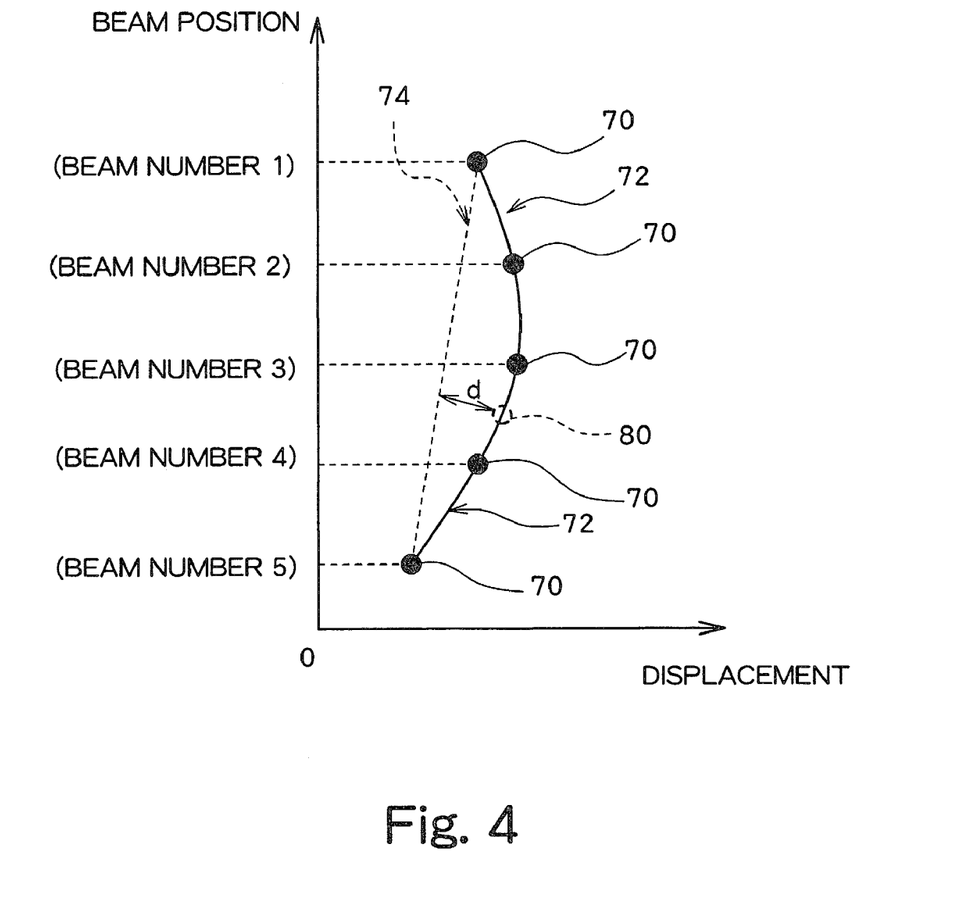
FIG. 4 is a diagram for explaining a calculation method of an elasticity value of a bone.

FIG. 4 is a diagram for explaining a calculation method of the amount of strain of the bone. FIG. 4 shows a coordinate system having the beam position of the ultrasonic beam on the vertical axis and the displacement of the surface point on the horizontal axis. On the coordinate system, five measurement points 70 are pointed as points correlating the beam positions of the ultrasonic beams and the displacements measured for the ultrasonic beams. The beam positions are positions of the echo tracking ultrasonic beams (heights of the ultrasonic beams 40 in FIG. 1), and are identified with the beam numbers 1-5, in order from the top (from higher to lower).

In calculation of the amount of strain of the bone, first, an interpolation line 72 connecting five measurement points 70 is generated. The interpolation line 72 can be obtained by, for example, interpolating a curve for the five measurement points 70 using a spline interpolation or a least square interpolation. The degree of curvature of the interpolation line 72 is evaluated based on a comparison between a line 74 connecting two end points among the five measurement points 70 and the interpolation line 72. More specifically, an amount of strain of the bone $\gamma=d/L$ is calculated from the length L of the line 74 and a distance d between the line 74 and a maximum displacement point 80 which is on the interpolation line 72 existing at a point furthest away from the line 74.

For the measurement of the amount of strain of the bone, the method described in JP 2004-298205 A may be utilized. In other words, an interpolation line connecting the plurality of surface points of the bone in the measurement state may be generated and the amount of strain of the bone may be calculated based on the interpolation line. As detailed in JP 2004-298205 A, the amount of strain of the bone $\gamma=\Delta d/L$ may be calculated by overlapping the interpolation line of the no-load state and the interpolation line of the loaded state so that the ends match, and based on a maximum displacement $\Delta d$ between the two interpolation lines and the length L of the interpolation line.

In the present embodiment, the amount of strain $\gamma$ of the bone is measured for each state with a different load. A method of applying the load on the bone will now be described.

Figure 5:
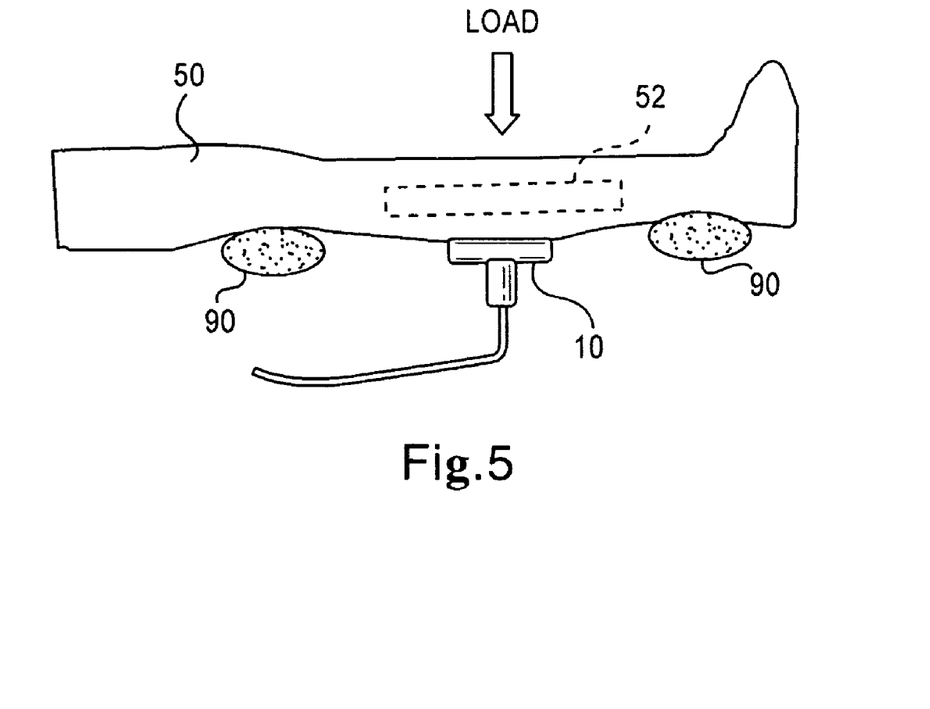
FIG. 5 is a diagram for explaining application of a load on a bone.

FIG. 5 is a diagram for explaining application of the load on the bone, and shows the subject 50 and the bone 52 in the body of the subject 50. The bone 52 may be, for example, a tibia, a lower limb bone of the lower leg. As shown in FIG. 5, the subject (leg) 50 is fixed with two fixing pads 90 from the lower part of the figure, and a load is applied near the center between the two fixing pads 90 from the upper part of the figure. As a result, a three-point load is applied to the bone 52. The probe 10 is contacted on the surface of the subject 50 near the center between the two fixing pads 90 from the lower part of the figure, and the probe 10 forms ultrasonic beams toward the bone 52.

The manner of application of the load to the bone 52 is not limited to the three-point loading method of FIG. 5. For example, the load may be applied to one point while the subject 50 stands. In addition, the position of the probe 10 may be shifted to left and the right (upward and downward directions of the leg) from the position of FIG. 5 in a degree to allow confirmation of the deformation of the bone 52 due to the load.

The load on the bone 52 may be approximately 25 N (Newtons) for a sufficient evaluation when the target bone is a healthy bone. With the load of approximately 25 N to a healthy bone, normally, there is no problem with respect to the invasiveness. When the target bone is an abnormal bone such as a fractured bone, measures, such as reducing the amount of load, must be taken in consideration of the invasiveness.

In the present embodiment, an amount of strain $\gamma$ is measured for each of the states with different loads, and viscoelasticity of the bone is evaluated based on a degree of follow of the amount of strain of the bone with respect to the change of the load. First, the viscoelasticity of the bone will be described based on a model.

Figure 6:
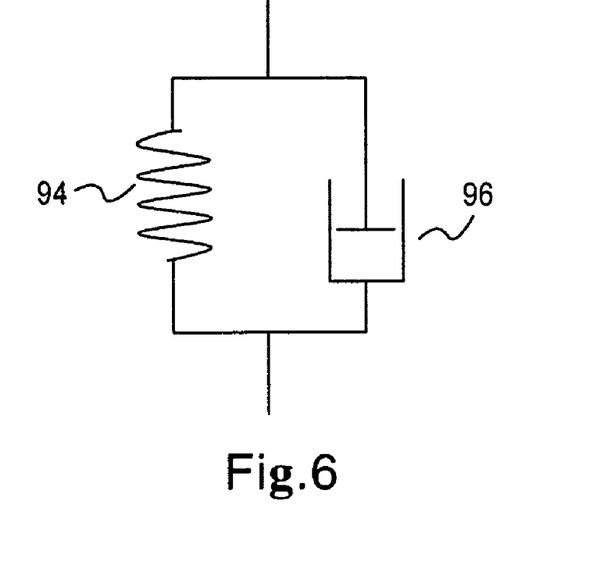
FIG. 6 is a diagram showing a viscoelastic model for explaining a viscoelasticity of a bone.

FIG. 6 is a diagram showing a viscoelasticity model for explaining the viscoelasticity of the bone. The viscoelasticity model of FIG. 6 is a model, known as a Voigt model, with a spring 94 which functions as an elastic structure and a dashpot 96 which functions as a viscous structure.

Figure 7A:
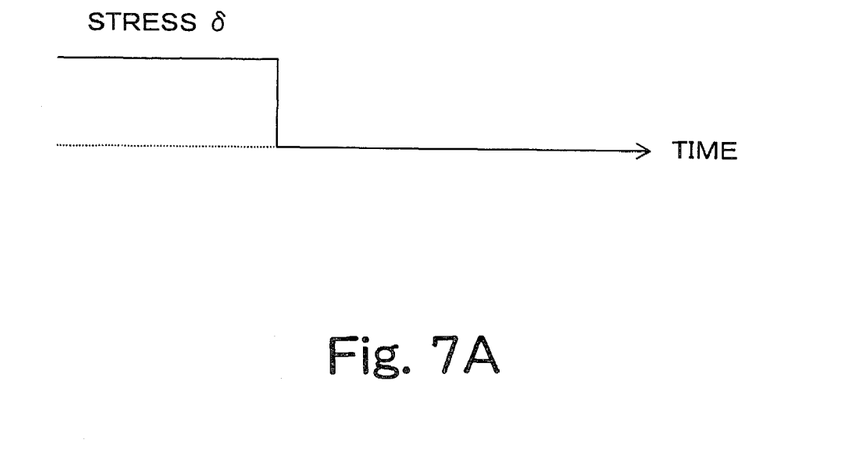
FIGS. 7A and 7B are diagrams for explaining a relationship between a stress and a strain of a bone in Voigt model.
Figure 7B:
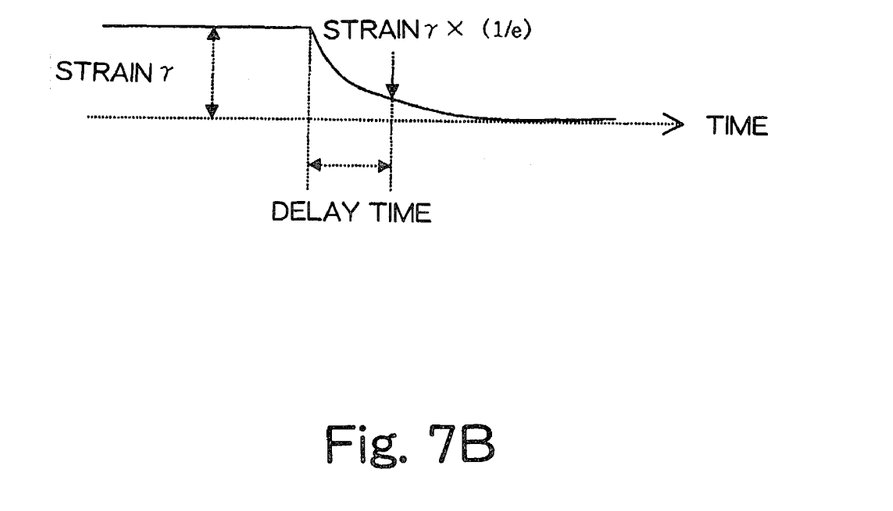

FIGS. 7A and 7B are diagrams for explaining a relationship between a stress and a strain of a bone in the Voigt model. FIG. 7A shows a change of stress with the horizontal axis being a time axis and FIG. 7B shows a change of the strain in the same time line as in FIG. 7A. In the Voigt model (FIG. 6), the dashpot (96) which functions as the viscous structure acts in a direction to inhibit the movement of the spring. Because of this, the strain of the bone in the Voigt model (corresponding to the displacement of the spring) changes with a delay compared to the change of the stress as shown in FIGS. 7A and 7B.

In a simple model such as the Voigt model, the time for the amount of strain to change from the amount of strain $\gamma$ in the reference state of application of the reference stress to 1/e (e is a base of natural logarithm) of $\gamma$ after the stress changes is referred to as delay time and is used as a parameter for evaluation of the viscoelasticity. In the present embodiment also, the delay time may be used as the parameter of the evaluation of the viscoelasticity. However, because the actual bone has a structure with a complex combination of the elastic structure and the viscous structure, a parameter different from the parameter of the simple Voigt model may be used. The evaluation of the viscoelasticity in the present embodiment will next be described in detail.

Figure 8:
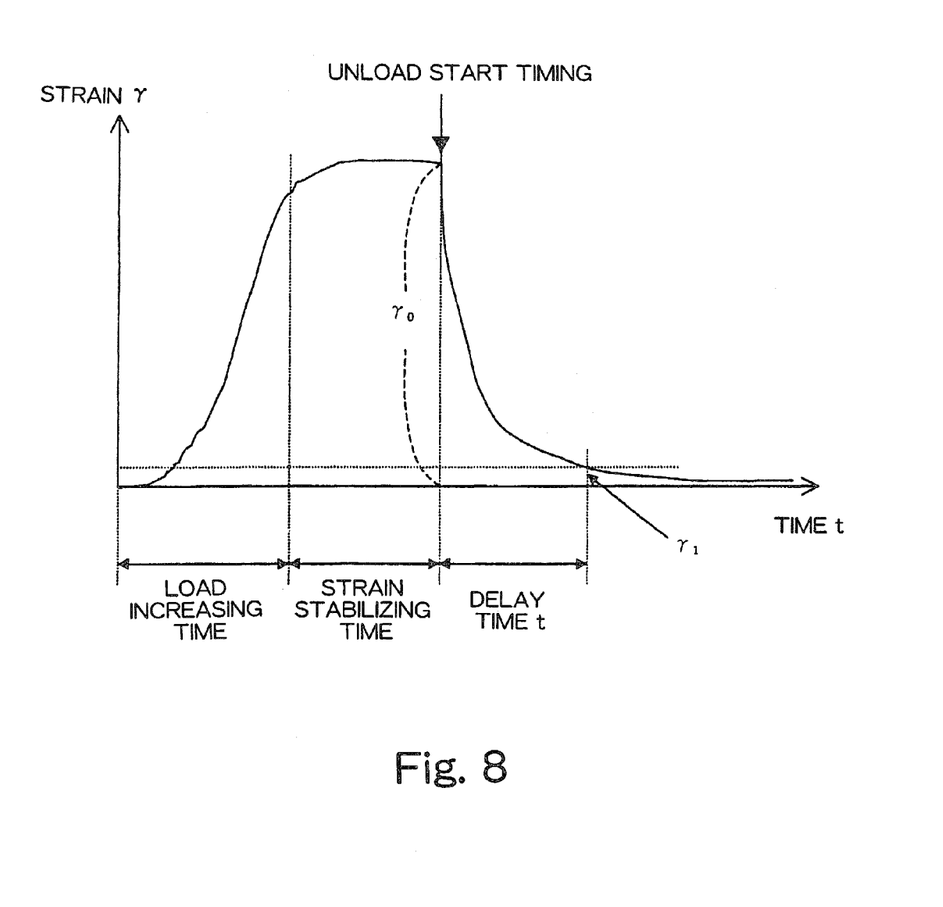
FIG. 8 is a diagram for explaining an evaluation method of a viscoelasticity in a preferred embodiment of the present invention.

FIG. 8 is a diagram for explaining an evaluation method of viscoelasticity in the present embodiment, and shows a graph having the time on the horizontal axis and the amount of strain $\gamma$ on the vertical axis. An evaluation method of the viscoelasticity will now be described with reference to FIG. 8. The structures shown in FIG. 1 are described using the reference numerals assigned in FIG. 1.

First, echo tracking of the surface point of the bone 52 is started from a state before the load is applied, that is, from the origin of the time axis in FIG. 8. As described above, the surface portion of the bone 52 is tracked primarily by the function of the echo tracking processor 20. The echo tracking is continued subsequently, and the amount of strain is measured by the strain measurement unit 22 for each state with a changed load.

Next, a load is slowly applied to the bone 52, in such a manner that the application is not invasive. In other words, the load is gradually increased in the load increasing time of FIG. 8. The load increasing time may be, for example, 10 seconds.

Next, after the target load value is reached, the amount of load is maintained for a predetermined amount of time. That is, the amount of load is maintained at a constant in a strain stabilizing time in FIG. 8. This is a process in consideration of a creep phenomenon of the bone 52 which is a viscoelastic structure (delay of strain with respect to a change of stress). During this process, by observing the movement of the bone surface with echo tracking, it is possible to check the completion of the creep phenomenon (stabilization of amount of strain). The strain stabilizing time may be, for example, 10 seconds.

When the amount of strain is stabilized, the load is completely removed at an unload start timing of FIG. 8. When the load is removed, the bone 52 gradually returns to the state before the load is applied because the bone 52 has the viscoelastic characteristic. During this process, a delay time measurement unit 24 measures a delay time t for the amount of strain of the bone 52 to return from the maximum amount of strain $\gamma_0$ at the loaded state to a return reference value $\gamma_1$ (which is a % of $\gamma_0$, for example, 5% of $\gamma_0$). The delay time t measured in this manner is taken as the evaluation value reflecting the viscoelasticity of the bone 52.

For example, when it is determined, as a result of comparison of a delay time $t_1$ of a healthy bone and a delay time $t_2$ of a measurement target bone, that $t_1 > t_2$, the measurement target bone can be evaluated to have a lower viscosity compared to the healthy bone. Because of this, the measurement target bone can be determined to be, for example, a fragile bone lacking flexibility with respect to an impact, and a condition of osteoporosis may be suspected. When, on the other hand, $t_2 > t_1$, the measurement target bone has a lower elasticity (rigidity) than the healthy bone. Because of this, for example, a condition such as rickets (a disease in which deposition of calcium on the bone is insufficient and the bone does not have the hardness in a level of the healthy bone) may be suspected for the measurement target bone.

In this manner, the evaluation focused on the viscoelasticity of the bone is enabled, and, as a consequence, clinically useful information can be obtained. In FIG. 8, the delay time t for the amount of strain to return from the maximum amount of strain $\gamma_0$ to the return reference value $\gamma_1$ (a % of $\gamma_0$) is measured. The value of the ratio a for obtaining the return reference value $\gamma_1$ is suitably set according to the type of the bone and condition to be checked. Alternatively, similar to the Voigt model, the time for the amount of strain to change to 1/e of $\gamma_0$ (e is a base for the natural logarithm) may be set as the delay time.

Referring again to FIG. 1, when the delay time is measured by the delay time measurement unit 24 in the manner as described above, the measured delay time is sent to a display image formation unit 32. The cross sectional image data formed in the cross sectional image formation unit 18 is also supplied to the display image formation unit 32. The display image formation unit 32 forms a cross sectional image of a bone based on the cross sectional image data and causes the image to be displayed on a display 34. In addition, data of the amount of strain of the bone at each time measured in the strain measurement unit 22 is also supplied to the display image formation unit 32. Based on the data of the amount of strain, the display image formation unit 32 forms an image showing the amount of strain of the bone at each time, for example, a graph as shown in FIG. 8 having the horizontal axis as time and vertical axis as the amount of strain, and causes the image to be displayed on the display 34. In addition, the value of the delay time measured by the delay time measurement unit 24 is displayed. The cross sectional image of the bone, the graph of the amount of strain, and the value of the delay time may be simultaneously displayed or may be displayed in a switching manner according to a selection operation performed by the examiner or the like.

As described, with the preferred embodiment of the present invention, the viscoelasticity of the bone can be evaluated. Alternatively, a periodic load may be repeatedly applied to the bone, the amount of strain may be measured, and the hysteresis characteristic between the amount of load and the amount of strain may be obtained, so that the viscoelasticity of the bone can be evaluated based on an area of the hysteresis loop or the like. However, in order to obtain the hysteresis characteristic, the load must be periodically (dynamically) applied, and the loading mechanism or the like becomes complex. In addition, the repeated application of the load to a subject causes a large burden to the subject.

In the above-described preferred embodiment of the present invention, on the other hand, repeated application of the load is not necessary, and, thus, this method can be considered as evaluation of static viscoelasticity of the bone. In the preferred embodiment of the present invention, because it is not necessary to repeatedly apply a load, the mechanism for applying the load can be simplified. Moreover, because the repeated load to the subject can be avoided, substantially non-invasive evaluation is possible.

In the preferred embodiment of the present invention, because the evaluation value for evaluating the viscoelasticity is the delay time which is a scalar amount, it is not necessary to precisely measure the direction of change of the strain. Because of this, there is an advantage that reproducible data can be easily obtained even when the position of the probe is not precisely adjusted.

A preferred embodiment of the present invention has been described. However, the above-described preferred embodiment is merely exemplary, and the scope of the present invention is not limited to the above-described preferred embodiment.

For example, in the above-described example, the amount of strain is measured by the strain measurement unit (reference numeral 22 in FIG. 1) as the shape value for evaluation of the viscoelasticity. However, the shape value for evaluation of viscoelasticity may be other measurement values reflecting the viscoelasticity. For example, the evaluation value may be a displacement of a surface point on a certain ultrasonic beam. In other words, by continuously measuring a displacement of a surface point on a certain ultrasonic beam in response to the change of the load, it is possible to obtain a graph in which the vertical axis of FIG. 8 is changed from the strain $\gamma$ to the displacement d. Similar to the case of the strain $\gamma$, in the case where the vertical axis is changed to the displacement d also, the delay time t for the displacement d to return from the maximum displacement $d_0$ in the loaded state to the return reference value $d_1$ (a % of $d_0$) is measured as the evaluation value reflecting the viscoelasticity.

What is claimed is:

1. An ultrasound diagnosis apparatus comprising:
   a transmission and reception unit which forms an ultrasonic beam on a hard tissue and obtains an echo signal;
   a surface detecting unit which detects a plurality of surface points corresponding to a surface of the hard tissue based on the echo signal;
   a shape value measurement unit which measures a shape value reflecting a shape of the hard tissue based on the plurality of detected surface points; and
   an evaluation value measurement unit which measures an evaluation value of a mechanical characteristic of the hard tissue based on a return change of the shape value from a state in which a load is applied to the hard tissue to a state after the load is completely removed, wherein
   the evaluation value measurement unit measures, as the evaluation value, a time for the shape value to reach, after the load is removed from the state of application of the load to the hard tissue, a return reference value corresponding to a state before the load is applied.

2. The ultrasound diagnosis apparatus according to claim 1, wherein the return reference value is set based on a maximum shape value which is a shape value in a state in which the load is applied to the hard tissue.

3. An ultrasound diagnosis apparatus comprising:
   a transmission and reception unit which forms an ultrasonic beam on a bone within a living body and obtains an echo signal;
   a surface detecting unit which detects a plurality of surface points corresponding to a surface of the bone based on the echo signal;

a shape value measurement unit which measures a shape value reflecting a shape of the bone based on the plurality of detected surface points; and an evaluation value measurement unit which measures an evaluation value of a mechanical characteristic of the bone based on a return change of the shape value from a state in which load is applied to the bone to a state after the load is completely removed, wherein the evaluation value measurement unit measures, as the evaluation value, a time for the shape value to reach a return reference value, corresponding to a state before the load is applied, after the load is removed from a state in which the load is applied to the bone.

4. The ultrasound diagnosis apparatus according to claim 3, wherein
the surface detecting unit detects a plurality of surface points corresponding to the surface of the bone based on the echo signal and tracks each of the surface points following a movement of each of the surface points; and
the shape value measurement unit measures the shape value based on the plurality of tracked surface points.

5. The ultrasound diagnosis apparatus according to claim 4, wherein
the surface detecting unit tracks each of the surface points by an echo tracking process when tracking the plurality of surface points.

6. The ultrasound diagnosis apparatus according to claim 4, wherein
the shape value measurement unit measures, as the shape value, the amount of strain of the surface of the bone based on the plurality of tracked surface points.

7. The ultrasound diagnosis apparatus according to claim 6, wherein
the evaluation value measurement unit measures, as the measurement value, a time for an amount of strain to reach a return reference value corresponding to a state in which no load is applied after a load is slowly applied to the bone by gradually increasing the load in a load increasing time, the applied load reaches a target amount of load, the amount of load is maintained at a constant in a strain stabilizing time, the amount of strain is stabilized, and the load is removed.

8. The ultrasound diagnosis apparatus according to claim 7, wherein
the return reference value is set based on a maximum amount of strain in a state in which the load is applied to the bone.

9. The ultrasound diagnosis apparatus according to claim 8, wherein
the return reference value is set as a percentage of the maximum amount of strain.

10. The ultrasound diagnosis apparatus according to claim 8, wherein
the return reference value is set at 1/e (where e is a base of natural logarithm) of the maximum amount of strain.

11. The ultrasound diagnosis apparatus according to claim 6, wherein
the shape value measurement unit calculates, based on a comparison between a straight line connecting two ends among the plurality of tracked surface points and an interpolation line connecting the plurality of surface points, the amount of strain of the bone surface based on a degree of curvature of the interpolation line.

12. The ultrasound diagnosis apparatus according to claim 11, wherein
the shape value measurement unit calculates, based on a distance d between the straight line and a maximum displacement point which is a point on the interpolation line existing at a position furthest away from the straight line, an amount of strain of the bone $\gamma=d/L$ from a length L of the straight line and the distance d.

13. The ultrasound diagnosis apparatus according to claim 6, wherein the shape value measurement unit calculates an amount of strain of the bone $\gamma=\Delta d/L$ based on a maximum amount of displacement $\Delta d$ between two interpolation lines using interpolation lines connecting the plurality of surface points and overlapping an interpolation line at the no-load state and an interpolation line at a loaded state so that the ends of the interpolation lines match and a length L of the interpolation line.

14. The ultrasound diagnosis apparatus according to claim 4, wherein
the shape value measurement unit measures an amount of displacement at each surface point as the shape value.

* * * * *